United States Patent

Kores et al.

[11] Patent Number: 5,362,708
[45] Date of Patent: Nov. 8, 1994

[54] HERBICIDAL AGENT

[75] Inventors: Dietmar Kores, Leonding; Hermann Tramberger, Seitenstetten; Rudolf H. Wörther; Rudolf Jellinger, both of Linz; Engelbert Kloimstein, Eferding; Rupert Schönbeck, Leonding, all of Austria

[73] Assignee: Agrolinz Agrarchemikalien GmbH, Linz, Austria

[21] Appl. No.: 960,292

[22] Filed: Oct. 13, 1992

Related U.S. Application Data

[63] Continuation of Ser. No. 668,477, Mar. 13, 1991, abandoned.

[30] Foreign Application Priority Data

Apr. 5, 1990 [AT] Austria ................................. A807/90

[51] Int. Cl.$^5$ ........................................... A01N 43/58
[52] U.S. Cl. ..................................................... 504/238
[58] Field of Search ........................................ 504/238

[56] References Cited

U.S. PATENT DOCUMENTS

| | | | |
|---|---|---|---|
| 3,932,405 | 1/1976 | Schonbeck et al. | 71/92 |
| 3,953,445 | 4/1976 | Schonbeck et al. | 71/92 |
| 4,067,723 | 1/1978 | Garland et al. | 71/92 |
| 4,279,908 | 7/1981 | Jojima et al. | 424/248.55 |
| 4,623,376 | 11/1986 | Speltz et al. | 71/92 |

FOREIGN PATENT DOCUMENTS

| | | |
|---|---|---|
| 56-113767 | 9/1981 | Japan . |
| 59-01469 | 1/1984 | Japan . |
| 59-212479 | 12/1984 | Japan . |

OTHER PUBLICATIONS

Weissberger et al., The Chemistry of Heterocyclic Compounds, vol. 28, p. 32.
Auer et al., Chemical Abstracts, vol. 85, p. 143 (1976) Abstract No. 138437j.
Zugravescu et al., Chemical Abstracts, vol. 93 (1980) Abstract No. 8198m.
Harris et al., Chemical Abstracts, vol. 95, p. 211 (1981) Abstract No. 36936k.
Nippon Soda, Chemical Abstracts, vol. 101, p. 712 (1984) Abstract No. 130699z.
Agricultural Chemicals-Book II Herbicides, 1983–1984 Revision, Fresno, CA, Thomson Publications, p. 104.
The Agrochemicals Handbook, second edition, Old Working, Surrey, Unwin Brothers Limited, 1983, p. A358/Aug. 1987.
Chemical Abstracts 117: 228381v (Dec. 7, 1992); abstracting Gressel, J. et al., "Pyridate is not a two-site inhibitor, and may be more prone to evolution of resistance than other phenolic herbicides" Pestic. Biochem. Physiol., vol. 44(2), 1992, pp. 140–146.

Primary Examiner—Richard L. Raymond
Assistant Examiner—John D. Pak
Attorney, Agent, or Firm—Wenderoth, Lind & Ponack

[57] ABSTRACT

A method for combatting weeds by applying to the weeds or their environment, a phenylpyridazine, wherein the phenyl group is substituted by hydroxy, halogen, cyano, nitro, amino, alkyl, alkoxy, cycloalkyl, cycloalkoxy, phenyl, phenoxy, alkylthio or an alkylsulfonyl group and wherein the pyridazinyl ring is substituted in the 4-position by hydroxy or by a —O—C(O)— derivative.

2 Claims, No Drawings

HERBICIDAL AGENT

This application is a continuation of now abandoned application Ser. No. 07/668,447 filed Mar. 13, 1991.

The invention relates to a herbicidal agent containing at least one substituted phenylpyridazine derivative.

JP-A 84/212,479 discloses herbicidally active 3-arylpyridazines which have an alkyl or dialkyl or alkylalkoxy or dialkylalkoxyamino group in the 5-position on the pyridazine ring.

JP-A 81/113,767 furthermore discloses substituted aryl-4(O-acyl)-6-halopyridazines which have a fungicidal activity.

Surprisingly, it has now been found that such substituted phenylpyridazine derivatives as are described in JP-A 81/113,767 have an excellent herbicidal activity.

The invention accordingly relates to herbicidal agents, characterized in that they contain at least one compound of the formula

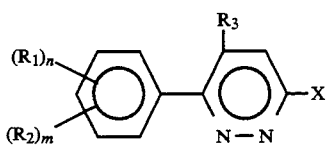

in which $R_1$ and $R_2$ independently of one another in each case represent hydroxyl, halogen, cyano or nitro groups or represent amino groups which are unsubstituted or are substituted by alkyl having 1–4 C atoms or represent straight-chain or branched alkyl having 1–10 C atoms which are unsubstituted or are monosubstituted or polysubstituted by hydroxyl, halogen or cyano groups or represent straight-chain or branched alkoxy having 1–10 C atoms, cycloalkyl having 5–7 C atoms, cycloalkoxy having 5–7 C atoms, phenyl, phenoxy, alkylthio or alkylsulfonyl having 1–4 C atoms, n and m independently of one another in each case represent the numbers 0, 1, 2 or 3, with the proviso that n+m is an integer of 1 to 5, $R_3$ represents the groups hydroxyl, —OC(O)ZR$_4$ or —OC(O)NR$_4$R$_5$ where $R_4$ represents a straight-chain or branched, saturated or unsaturated alkyl group having 1–15 C atoms and which is unsubstituted or is substituted by a phenyl group, or represents a phenyl group or a cycloalkyl group having 5–7 C atoms, $R_5$ represents a straight-chain or branched, saturated or unsaturated alkyl group having 1–15 C atoms and which is unsubstituted or is substituted by a phenyl radical, or represents a phenyl group or a cycloalkyl group having 5–7 C atoms, Z represents a single bond, oxygen or sulfur and X represents halogen, or its phytophysiologically acceptable salts.

In formula I, $R_1$ and $R_2$ independently of one another represent hydroxyl, a cyano group, a nitro group, an amino group which is unsubstituted or is substituted by alkyl having 1–4 C atoms, such as a methylamino, ethylamino, propylamino, butylamino, a dimethylamino, diethylamino, methylethylamino group or the like, or represent a halogen atom, for example a chlorine, bromine or fluorine atom. Furthermore, $R_1$ and $R_2$ independently of one another can represent a straight-chain or branched alkyl group having 1–10 C atoms, for example a methyl, ethyl, propyl, butyl, pentyl, hexyl, heptyl, octyl, nonyl or decyl group or their branched analogs, such as an i-propyl, i-butyl, t-butyl group or the like. These alkyl groups can be monosubstituted or polysubstituted by hydroxyl, cyano or halogen, for example chlorine, bromine or fluorine. Examples of such groups are cyanoalkyl groups, such as the cyanomethyl group, hydroxyalkyl groups such as the hydroxyethyl group, or haloalkyl groups such as the chloromethyl group, the bromomethyl group or the trifluoromethyl group. Furthermore, $R_1$ and $R_2$ independently of one another can represent an alkoxy group having 1–10 C atoms in the alkyl chain, for example a methoxy, an ethoxy, a propoxy, a butoxy group or the like, or a cycloalkyl group having 5–7 C atoms such as a cyclopentyl, cyclohexyl or cycloheptyl group, or a phenyl radical or a phenoxy radical. Furthermore, $R_1$ and $R_2$ can in each case represent an alkylthio radical having 1–4 C atoms in the alkyl chain such as a methylthio, ethylthio, propylthio or butylthio group, or an alkylsulfonyl group having 1–4 C atoms, for example a methylsulfonyl group.

n and m in each case represent the numbers 0, 1, 2 or 3, with the proviso that n+m is an integer of 1 to 5.

Preferred compounds are those in which $R_1$ and $R_2$ in each case represent a halogen atom, for example chlorine, bromine or fluorine, and n+m is 1 or 2 or an alkyl group which has 1–4 C atoms and which is unsubstituted or is monosubstituted or polysubstituted by halogen, preferably by chlorine or fluorine, and n+m is 1 or 2, or an alkoxy group having 1–4 C atoms in the alkyl chain, or a cyclohexyl group.

Particularly preferred compounds are those in which $R_1$ and $R_2$ represent a halogen atom, for example chlorine or fluorine, n+m being 1 or 2, or a trifluoromethyl group, n+m being the number 1.

$R_3$ represents hydroxyl or the group —OC(O)ZR$_4$, or the group —OC(O)NR$_4$R$_5$, where $R_4$ represents a straight-chain or branched, saturated or unsaturated alkyl group having 1–15 C atoms, for example a methyl, ethyl, propyl or butyl, pentyl, heptyl, decyl, dodecyl or pentadecyl radical or their branched analogs, which can be unsubstituted or substituted by a phenyl radical. Furthermore, $R_4$ can represent a phenyl group or a cycloalkyl group having 5–7 C atoms, for example the cyclohexyl group. $R_5$ represents a straight-chain or branched, saturated or unsaturated alkyl group having 1–15 C atoms, for example a methyl, ethyl, propyl or butyl, pentyl, heptyl, decyl, dodecyl or pentadecyl group or their branched analogs, and which can be unsubstituted or substituted by a phenyl group. $R_5$ can furthermore represent a phenyl group or a cycloalkyl group having 5–7 C atoms, for example the cyclohexyl group. The groups $R_4$ and $R_5$ can be identical or different. Preferred compounds are those in which $R_3$ represents the group —OC(O)ZR$_4$, $R_4$ and Z having the abovementioned meaning. X represents halogen, preferably chlorine or bromine.

The compounds of the formula I can be prepared by
a) reacting an appropriately substituted 3-phenyl-6-pyridazinone of the formula II

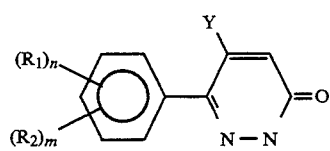

in which $R_1$, $R_2$, n and m have the abovementioned meaning and Y represents hydrogen or chlorine, with phosphorus oxyhalide and, in the event that Y represents hydrogen, additionally with phosphorus or $PCl_3$ or $PCl_5$ and a halogenating agent, to give the corresponding dihalogen compound of the formula III

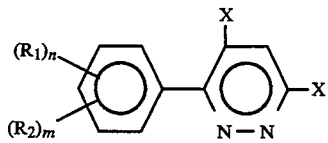

in which X has the abovementioned meaning, b) if desired, reacting this compound in the presence of a diluent and in the presence of a base to give the corresponding 3-phenyl-4-hydroxy-6-halopyridazine of the formula IV

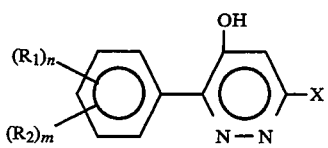

in which X has the abovementioned meaning, and subsequently, c) if appropriate, reacting this compound of the formula IV with an appropriate acid halide of the formula V or Va

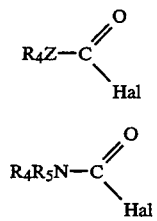

in which $R_4$, $R_5$ and Z have the abovementioned meaning, in the presence of an organic diluent and in the presence of a base, for example sodium hydroxide, potassium hydroxide or triethylamine, to give the compounds of the formula I in which $R_3$ does not represent hydroxyl and does not represent halogen.

However, the starting material in step a) can also be the corresponding 3-aryl-6-halopyridazine compound.

If $R_1$ or $R_2$ represents a nitro group, this group can, if desired, also be introduced before carrying out reaction step c) by nitrating the corresponding 3-aryl-4-hydroxy-6-halopyridazine compound. However, it is also possible to employ the appropriately substituted 6-pyridazinone as early as in step a).

The substituted 3-phenyl-6-pyridazinones which are required as starting compounds are obtained in a manner known per se from the corresponding acetophenone by reaction with glyoxylic acid and hydrazine, or from the corresponding benzoylacrylic acid by reaction with a lower aliphatic alcohol in the presence of a catalyst, followed by reaction with hydrazine, or from the corresponding benzoylacrylic acid by esterification with a lower aliphatic alcohol in the presence of an esterification catalyst, followed by reaction with hydrazine, or by reaction of the corresponding benzoyl acrylic acids with $NH_3$ and hydrazine.

The compounds of the formula II in which Y represents Cl can be prepared by the method of Weissberger A., Taylor E. C. (editor), The Chemistry of Heterocyclic Compounds Vol. 28, p. 32. The reaction to give the dihalogen compounds is carried out in the presence of phosphorus oxyhalide and, if Y represents H, additionally by reaction with phosphorus or $PCl_3$ or $PCl_5$ and a halogenating agent. The dihalogen compounds are subsequently reacted to give the compounds of the formula IV, if appropriate in the presence of a diluent, for example a dioxane/water mixture, tetrahydrofuran and the like, and in the presence of a base, for example an alkali metal hydroxide such as sodium hydroxide solution or potassium hydroxide solution.

The acylation step which may subsequently follow, in which the compounds are reacted with an acid halide of the formula V or Va, is carried out in the presence of an organic diluent, for example in aqueous acetone, toluene or benzene and the like, and in the presence of a base. Suitable bases are inorganic bases, for example sodium hydroxide, potassium hydroxide, or organic bases, such as triethylamine.

The amine salts of the hydroxy compounds of the formula I in which $R_3$=OH are expediently prepared directly in a suitable formulation agent with the addition of a wetting agent. For example, a 50% strength preparation of the triethylamine salt of the compound of the formula I, $R_1$=4-Cl, $R_2$=H, $R_3$=OH, X=Cl, was prepared by suspending the hydroxy compound (substance 1, 3,526 g, 0.0146 mol) in a mixture of glycerol (4,445 g) and Rapidnetzer-Linz (0.500 g), followed by slow dropwise addition of triethylamine (1.527 g, 0.01509 mol, 3.2% excess). The mixture was then heated gently for 2 hours, during which process the temperature was raised from 40° C. to 60° C. This resulted in the formation of a homogeneous, 50% strength ready-to-use mixture of triethylamine salt.

The compositions according to the invention are suitable for controlling dicotyledon, but also monocotyledon, seed-propagated weeds in crops such as cereals, corn, peanuts, Brassicaceae, chick peas, tomatoes and onions.

They are particularly suitable for controlling
Amaranthus retoflexus
Anthemis arvensis
Centaurea arvensis
Chenopodium ficifolium
Echinochloa crus-galli
Galium aparine
Mercurialis annua
Lapsana communis
Panicum millaceum
Setaria glauca
Solanum americanum
Solanum nigrum
Stellaria media
in the abovementioned crops.

The compositions according to the invention can be formulated in the customary manner, for example as solutions, wettable powders, emulsion concentrates, emulsions, suspensions, dispersions, dusts, granules and the like, and in these cases they contain, if desired, the customary formulation auxiliaries such as extenders, that is to say liquid solvents, solid or liquid carriers, if appropriate with the use of surfactants, that is to say emulsifiers and/or dispersants and/or wetting agents, grinding auxiliaries, adhesives and the like. When water is used as the extender, it is also possible to use organic solvents as auxiliary solvents. The following are mainly suitable as liquid solvents: aromatics such as xylene, toluene and other alkylbenzenes or alkylnaphthalenes, chlorinated aromatics or chlorinated aliphatic hydrocarbons, such as chlorobenzenes, chloroethylenes or methylene chloride, cycloaliphatic hydrocarbons such as cyclohexane or paraffins, for example mineral oil fractions, alcohols such as butanol or glycol as well as their ethers and esters, ketones such as acetone, methyl ethyl ketone, methyl isobutyl ketone or cyclohexanone, strongly polar solvents such as dimethylformamide or dimethyl sulfoxide, and also water.

Wettable powders are preparations which are uniformly dispersible in water and which, besides the active substance, also contain wetting agents, for example polyoxethylated alkylphenols, polyoxethylated oleyl- or stearylamines, alkyl- or alkylphenylsulfonates, and dispersants, for example sodium oleyl methyl tauride, ligninsulfonates, or condensation products of arylsulfonates with formaldehyde, in addition to diluents or inert substances, which may be desired.

Emulsifiable concentrates can be prepared, for example, by dissolving the active substance in an organic solvent with the addition of one or more emulsifiers. Examples of suitable emulsifiers are non-ionic and ionic surfactants such as polyoxyethylene sorbitan tall oil esters, polyoxyethylene fatty acid esters, polyoxyethylene fatty alcohol ethers, alkylaryl polyglycol ethers, alkylsulfonates, alkyl sulfates and arylalkyl sulfonates, and also protein hydrolysates.

Dusts are obtained by grinding the active substance with finely-divided solid substances such as ground natural minerals, for example kaolins, clay, talc, chalk, quartz, attapulgite, montmorillonite or diatomaceous earths, and synthetic products such as highly-disperse silica, alumina and silicates. Examples of suitable carriers for granules are crushed or fractionated natural minerals such as calcite, marble, pumice, sepiolite, dolomite, and also synthetic granules of inorganic and organic meals, and granules of organic materials such as sawdust, coconut shells, maize cobs and tobacco stalks. Adhesives and thickeners such as carboxymethylcellulose, methylcellulose, natural and synthetic polymers in the form of powders, granules and latices, such as gum arabic, polyvinyl alcohol and polyvinyl acetate, can be used in the formulations.

Colorants such as inorganic pigments, for example iron oxide, titanium oxide, Prussian Blue, and organic dyestuffs such as alizarin and phthalocyanine dyestuffs, can be used.

In general, the formulations contain between 0.1 and 95% by weight of active substance, preferably between 0.5 and 90% by weight.

The active substances can be applied as such, in the form of their formulations or in the form of the use forms prepared therefrom by further dilution, such as ready-to-use solutions, emulsions, suspensions, powders and granules. They are applied in a customary manner, for example by pouring, spraying, atomizing, dusting, broadcasting and the like.

The necessary application rate of compositions according to the invention varies with the external conditions such as temperature, humidity and the like. It can range within wide limits and is generally between 0.2 and 10 kg of active substances/ha, preferably 0.3–1.5 kg/ha.

EXAMPLE 1

Preparation of the starting compound 3-(4'-Fluorophenyl)-6-pyridazinone a) From p-fluoroacetophenone with glyoxylic acid and hydrazine:

4'-Fluoroacetophenone (138.1 g, 1 mol) and glyoxylic acid monohydrate (27.5 g, 0.3 mol) were mixed and the mixture was stirred for 1.75 hours at 105° C. It was then cooled to 60° C., partitioned between water (500 ml) and Inhibisol (400 ml), and the pH of the aqueous phase was brought to pH 9 using NH$_4$OH solution. The separated phases were then again washed, mutually, with Inhibisol (200 ml) or with highly dilute NH$_4$OH solution (pH 9, 400 ml), and the combined aqueous phases (pH about 8.5) were treated with hydrazine hydrate (16.5 g), refluxed for 4 hours, concentrated (400 ml of distillate) and cooled to 0°, and the resulting crystallizate was isolated, washed with water and dried to constant weight. 3-(4'-Fluorophenyl)-6-pyridazinone (48.0 g, 0.2524 mol, 84.5% of theory) of m.p.=264°–269° C. was obtained. Recrystallized from a mixture of DMF and ethanol, the product showed a m.p. of 268°–270° C.

b) From (4'-fluorobenzoyl)-acrylic acid:

(4'-Fluorobenzoyl)-acrylic acid (582 g, 2.998 mol of m.p.=134°–137° C.) was dissolved in ethanol (3300 ml), p-toluenesulfonic acid (23 g) and sulfuric acid (conc., 4 ml) was added, and the mixture was then refluxed for 18 hours. The mineral acid was then neutralized by adding anhydrous sodium bicarbonate. The inorganic salts were then filtered off, a hydrazine solution (6 mol hydrazine, 700 ml of water) was added to the mechanically stirred solution of the esterification product, and the mixture was refluxed for three hours. A solid product precipitated, and this product was isolated, washed with water, mixed with dilute hydrochloric acid (700 ml of concentrated HCl, 1600 ml of water) while still moist from filtration with suction, and the mixture was refluxed for 2 hours. The mixture was cooled, and the resulting solid product was isolated, washed with water and dried to constant weight. 3-(4'-Fluorophenyl)-6-pyridazinone was obtained in the form of a yellowish solid product (390 g, 2.0508 mol, 68.4% of theory) of m.p.=266°–269° C. Recrystallization from dioxane gave a virtually colorless product which sublimes from about 170° C. in the form of broad crystals and which melts at 269°–270.5° C.

c) From (4'-fluorobenzoyl)alanine:

3-(4'-Fluorobenzoyl)-acrylic acid (9.7 g, 0.04996 mol) was dissolved in 50 ml of concentrated aqueous ammonia solution, and the solution was allowed to stand for a few days, without a cover. The solution was first rendered neutral by adding hydrochloric acid (concentrated, 30 ml), a further 20 ml of concentrated hydrochloric acid were then added, followed by hydrazine hydrochloride (4.1 g, 0.06 mol), after which the mixture was refluxed for 8 hours. After cooling, the solid product which had precipitated was isolated, washed with water and dried to constant weight. 3-(4'-Fluorophenyl)-6-pyridazinone of m.p.=265°–267° C., 8.9 g, 0.04680 mol, were obtained, which corresponds to a yield of 93.7% of theory.

EXAMPLE 2

Compound No. 68

3-(4'-Fluorophenyl)-4,6-dichloropyridazine 3-(4'-Fluorophenyl)-6-pyridazinone (190 g, 0.9991 mol) was mixed with red phosphorus (40 g, 1.291 mol), after which 1300 ml of phosphorus oxychloride were added. The suspension was then brought to 90° C. in the course of one hour, and an average stream of chlorine was then passed into the solution. The temperature of the reaction mixture rose to 100° C., and this temperature was maintained. The mixture was chlorinated for 4 hours, the dissolved gases were then expelled by passing in an average stream of nitrogen, 800 ml of phosphorus oxychloride were distilled off under a water pump vacuum, and the mixture was then decomposed on ice, during which process the resulting acid was neutralized with concentrated ammonia. This gave 235.2 g (0.9676 mol) of 3-(4'-fluorophenyl)-4,6-dichloropyridazine in the form of a solid product, which corresponds to a crude yield of 96.9%. Recrystallized from ethanol and cyclohexane, the product showed a melting point of 124°-127° C.

EXAMPLE 3

Compound No. 56

3-(4'-Fluorophenyl)-4-hydroxy-6-chloropyridazine 3-(4'-Fluorophenyl)-4,6-dichloropyridazine (145.84 g, 0.600 mol) was dissolved in dioxane (800 ml) at 60° C., water (300 ml) was added, and the solution was refluxed. Sodium hydroxide solution (48 g of solid NaOH, dissolved in 300 ml of water) was then added dropwise in the course of half an hour, and the mixture was kept under reflux for a further 5 hours. The mixture was then evaporated to dryness in vacuo, the residue was dissolved in hot water (5 l), insoluble particles were filtered off, and the solution was brought to pH 1 using concentrated hydrochloric acid. The solid obtained was isolated, washed with water and dissolved in dilute ammonia (8 l of water, pH 9–10) for further purification. Small amounts of 3-(4'-fluorophenyl)-4-chloro-6-pyridazinone were then selectively precipitated by carefully adding hydrochloric acid and then removed (by filtration), and the main bulk was then precipitated out (up to pH 1). The solid product obtained was isolated, washed with water and dried to constant weight. 91.0 g (0.4051 mol) of 3-(4'-fluorophenyl)-4-hydroxy-6-chloropyridazine of m.p.=254°-260° C. (point of decomposition) were obtained, which corresponds to a yield of 67.5% of theory.

EXAMPLE 4

Compound No. 64

3-(4'-Fluorophenyl)-6-chloro-4-(octylthiocarbonyloxy)pyridazine 3-(4'-Fluorophenyl)-4-hydroxy-6-chloropyridazine (22.5 g, 0.1 mol) was suspended in 80 ml of acetone. The solution of 4 g (0.1 mol) of sodium hydroxide in 80 ml of water was then added, and the solution, which was initially still cloudy, was heated at 60° C. To the solution, which was now clear, octyl thiochloroformate (20.97 g, 0.1 mol) was added all at once. The temperature of the solution rose as a consequence of the reaction, and an emulsion formed. The emulsion was kept under reflux for ¾ hour, and the pH, which had dropped to 6, was brought to 9 using 25% strength sodium hydroxide solution. The heavier organic phase of the resulting two-phase mixture was separated off and freed in vacuo from the volatile components. The crude ester obtained (brown oil, 36.7 g, crude yield 95%) was purified over a silica gel column, during which process the abovementioned compound was obtained in the form of a yellow oil ($n_D^{20}$=1.5567, 30.4 g, 79% of theory).

EXAMPLE 5

Compound No. 57

3-(4'-Fluorophenyl)-4-(propylthiocarbonyloxy)-6-chloropyridazine 3-(4'-Fluorophenyl)-4-hydroxy-6-chloropyridazine (22.4 g, 0.1 mol) was suspended in benzene (2000 ml) by stirring, triethylamine (10.1 g, 0.1 mol) was added, and the mixture was stirred for 3.5 hours at room temperature. Propyl thiocarbonate (13.86 g, 0.09999 mol) was then added dropwise in the course of 10 minutes. The temperature rose slightly, and the reaction mixture was stirred for a further 3 hours without heating. The triethylamine hydrochloride which had precipitated was filtered off, and the benzene phase was washed with in each case 2 100 ml portions of water, then highly dilute hydrochloric acid, then highly dilute sodium hydroxide solution, and then again with water. The organic phase was then dried over sodium sulfate and fined with animal charcoal, and all of the solvent was stripped off in vacuo, finally under an oil-pump vacuum, at a bath temperature of 90° C. 27.0 g (0.08263 mol) of 3-(4'-fluorophenyl)-4-(propylthiocarbonyloxy)-6-chloropyridazine remained in the form of a yellow oil, which corresponds to a yield of 82.9% of theory.

EXAMPLE 6

Compound No. 143

3-(4'-Bromophenyl)-4-(2,2-dimethylpropyloxycarbonyloxy)-6-chloropyridazine 3-(4'-Bromophenyl)-4-hydroxy-6-chloropyridazine (obtained analogously to Examples 1–3) (8.57 g, 0.03 mol) was suspended in benzene (90 ml), and triethylamine (3.19 g) was added. The solid product changed visibly. The mixture was stirred for 30 minutes, and a solution of 2,2-dimethylpropyl chloroformate (4.38 g, 0.0291 mol) in 20 ml of benzene was then added dropwise over 30 minutes. The temperature of the mixture rose slightly. After three hours, 20 ml of water were added, the mixture was stirred vigorously for 5 minutes, the benzene phase was then separated off and dried over sodium sulfate, and the solvent was removed in vacuo. The residue which remained solidified and was recrystallized twice from diisopropyl ether. 3-(4'-Bromophenyl)-4-(2,2-dimethylpropyloxycarbonyloxy)-6-chloropyridazine was obtained in the form of colorless crystal prisms of m.p.=114°-116° C. (6.7 g, 0.01676 mol, 57.6% of theory).

EXAMPLE 7

Compound No. 19

3-(4'-Chlorophenyl)-4,6-dibromopyridazine 3-(4'-Chlorophenyl)-4-hydroxy-6-chloropyridazine (Compound 1, 24.1 g, 0.09997 mol) was initially introduced into a reaction flask and a solution of phosphorus oxybromide (85.8 g, 0.3 mol) in toluene (150 ml) was added, and the reaction mixture was then stirred for one hour at room temperature. The mixture was then refluxed gently for three hours, during which process gaseous hydrogen bromide was given off. The mixture was decomposed on ice, which gave a pasty reaction product, which solidified on trituration with petroleum ether. The product was then washed thoroughly with water, isolated and dried to constant weight. 30.0 g (0.0861 mol, 86.1% of theory) of 3-(4'-chlorophenyl)-4,6-dibromopyridazine of m.p.=160°-162° C. were obtained. Recrystallized from an ethanol/dioxane mixture (20+3), the sample showed a melting point of 163°-165° C.

EXAMPLE 8

Compound No. 16

3-(4'-Chlorophenyl)-4-hydroxy-6-bromopyridazine 3-(4'-Chlorophenyl)-4,6-dibromopyridazine (52.2 g, 0.1498 mol) was dissolved in hot dioxane (300 ml) and a solution of 12 g (0.3 mol) of sodium hydroxide solution in 50 ml of water was added dropwise in the course of 10 minutes while the mixture was refluxed gently. The mixture was maintained under reflux for a further 4.5 hours, the dioxane was evaporated in vacuo, and the solid residue was dissolved in 1 l of hot water (95° C.). A small amount of solid product (tarry) was filtered under hot conditions with the aid of animal charcoal, and the hydrolysis product was precipitated using hydrochloric acid. The product which had been isolated (solid) by filtering off with suction was, while still moist, suspended in 1 l of water, after which process the pH of the suspension, at 65° C., was brought to 9-10 using ammonia. Most of the product dissolved, and the insoluble components were isolated and again treated with ammonia. The combined filtrates were then acidified using hydrochloric acid, and the 3-(4'-chlorophenyl)-4-hydroxy-6-bromopyridazine which was obtained was isolated, washed with water and dried to constant weight. 27.5 g, 0.09631 mol, 64.3% of theory, m.p.=262°-264° C. was thereby obtained.

EXAMPLE 9

Compound No. 17

3-(4'-Chlorophenyl)-4-(butylthiocarbonyloxy)-6-bromopyridazine 3-(4'-Chlorophenyl)-4-hydroxy-6-bromopyridazine (14.2 g, 0.0497 mol) was suspended in 100 ml of benzene, triethylamine (5.5 g, 0.0543 mol) was added, and the mixture was stirred for 3.5 hours at room temperature to complete the reaction. S-Butyl thiochlorocarbonate (7.85 g, 0.05162 mol) was then added dropwise to the mixture in the course of 5 minutes, and the reaction mixture was stirred for 3 more hours without heating. The triethylamine hydrochloride which had precipitated was filtered off, and the benzene solution was washed in succession in each case with 150 ml portions of water, highly dilute hydrochloric acid, highly dilute sodium hydroxide solution and then again water, and dried over sodium sulfate. The solvent was then removed completely in vacuo, and finally under an oil-pump vacuum (0.2 Torr, 90° C. bath temperature). The S-butyl thiocarbonate of 3-(4'-chlorophenyl)-4-hydroxy-6-chloropyridazine, which was first obtained as an oil (17.5 g, 0.04356 mol, 87.6% of theory), solidified upon prolonged standing and, when dissolved in and allowed to crystallize from hexane, showed amp. of 68°-71° C.

EXAMPLE 10

3-(3'-Nitro-4'-chlorophenyl)-4-hydroxy-6-chloropyridazine (Compound 138 )

3-(4'-Chlorophenyl)-4-hydroxy-6-chloropyridazine (12 g, 0.04978 mol) was introduced into cooled, highly-concentrated nitric acid in the course of 15 minutes at a temperature of 0°-5° C. The mixture was stirred for 30 more minutes at 0° C., and the reaction mixture was then stirred into ice-water. The resulting yellow solid product was isolated, washed with water and re-precipitated using NH$_4$OH/HCl. After drying, 11 g, 0.0385 mol, of 3-(3'-nitro-4'-chlorophenyl)-4-hydroxy-6-chloropyridazine of m.p. 204°-209° C. were obtained, which corresponds to a crude yield of 77.25%. According to TLC analysis (SiO$_2$/10% ethanol/chloroform), the sample proves to be largely uniform. Recrystallized from ethanol, the compound melts at 208°-211° C.

3-(3'-Nitro-4'-chlorophenyl)-4-butylthiocarbonyloxy)-6-chloropyridazine (Compound No. 88)

3-(3'-Nitro-4'-chlorophenyl)-4-hydroxy-6-chloropyridazine (14.3 g, 0.05 mol) was reacted in benzene with butyl thiochloroformate (7.88 g) and with triethylamine (5.05 g) as the hydrochloric acid binder by the customary method. 3-(3'-Nitro-4'-chlorophenyl)-4-(butylthiocarbonyloxy)-6 -chloropyridazine were obtained in the form of a pale brown oil. 17.0 g, 0.04226 mol, 84.55% of theory, n$_D^{20}$=1.6073.

| Comp. | R$_1$ | R$_2$ | n | m | R$_3$ | X | M.P.(°C.)/n$_D^{20}$ |
|---|---|---|---|---|---|---|---|
| 1 | 4-Cl | — | 1 | — | OH | Cl | 264-268* |
| 2 | 4-Cl | — | 1 | — | OC(O)C$_7$H$_{15}$-n | Cl | 40-43,5 |
| 3 | 4-Cl | — | 1 | — | OC(O)N(CH$_3$)$_2$ | Cl | 70-82 |
| 4 | 4-Cl | — | 1 | — | OC(O)OCH$_2$CH(CH$_3$)$_2$ | Cl | 72-74 |
| 5 | 4-Cl | — | 1 | — | O(CO)OC$_5$H$_{11}$-n | Cl | |
| 6 | 4-Cl | — | 1 | — | OC(O)SC$_3$H$_7$-n | Cl | 39-45 |
| 7 | 4-Cl | — | 1 | — | OC(O)SC$_4$H$_9$-n | Cl | 77,5-80 |
| 8 | 4-Cl | — | 1 | — | OC(O)SC$_4$H$_9$-t | Cl | 120-123 |
| 9 | 4-Cl | — | 1 | — | OC(O)SC$_5$H$_{11}$-n | Cl | 32-38 |
| 10 | 4-Cl | — | 1 | — | OC(O)SC$_6$H$_{13}$-n | Cl | |
| 11 | 4-Cl | — | 1 | — | OC(O)SC$_7$H$_{15}$-n | Cl | |
| 12 | 4-Cl | — | 1 | — | OC(O)SC$_8$H$_{17}$-n | Cl | 1,5733 |
| 13 | 4-Cl | — | 1 | — | OC(O)SC$_{12}$H$_{25}$-n | Cl | |
| 14 | 4-Cl | — | 1 | — | OC(O)SC$_6$H$_{11}$-c | Cl | |
| 15 | 4-Cl | — | 1 | — | OC(O)SC$_6$H$_5$ | Cl | 105-108 |
| 16 | 4-Cl | — | 1 | — | OH | Br | 262-264 |
| 17 | 4-Cl | — | 1 | — | OC(O)SC$_4$H$_9$-n | Br | 68-71 |
| 18 | 4-Cl | — | 1 | — | OC(O)SC$_8$H$_{17}$-n | Br | |
| 19 | 4-Cl | — | 1 | — | Br | Br | 163-165 |
| 20 | 4-Br | — | 1 | — | OH | Cl | 271-276 |
| 21 | 4-Br | — | 1 | — | OC(O)(CH$_2$)$_5$CH$_3$ | Cl | |
| 22 | 4-Br | — | 1 | — | OC(O)CH$_2$CH(CH$_3$)$_2$ | Cl | 49-56 |
| 23 | 4-Br | — | 1 | — | OC(O)C$_5$H$_{11}$-n | Cl | |
| 24 | 4-Br | — | 1 | — | OC(O)SC$_3$H$_7$-n | Cl | 75-77 |
| 25 | 4-Br | — | 1 | — | OC(O)SC$_4$H$_9$-sec | Cl | 71-73 |

-continued
Examples:

| Comp. | $R_1$ | $R_2$ | n | m | $R_3$ | X | M.P.(°C.)/$n_D^{20}$ |
|---|---|---|---|---|---|---|---|
| 26 | 4-Br | — | 1 | — | OC(O)SC$_4$H$_9$-t | Cl | 121–124 |
| 27 | 4-Br | — | 1 | — | OC(O)SC$_5$H$_{11}$-n | Cl | 57–59 |
| 28 | 4-Br | — | 1 | — | OC(O)SC$_5$H$_{11}$-i | Cl | 72–74 |
| 29 | 4-Br | — | 1 | — | OC(O)SC$_5$H$_{11}$-t | Cl | 75–88 |
| 30 | 4-Br | — | 1 | — | OC(O)SC$_7$H$_{15}$-n | Cl | 63–65 |
| 31 | 4-Br | — | 1 | — | OC(O)SC$_8$H$_{17}$-n | Cl | 45–47 |
| 32 | 4-Br | — | 1 | — | OC(O)SC$_{10}$H$_{21}$-n | Cl | 51–54 |
| 33 | 4-Br | — | 1 | — | OC(O)SC$_6$H$_{11}$-c | Cl | 69–73 |
| 34 | 3-Br | — | 1 | — | Cl | Cl | 112–114 |
| 35 | 3-Br | — | 1 | — | OH | Cl | 208–212 |
| 36 | 3-Br | — | 1 | — | OC(O)CH(C$_2$H$_5$)C$_4$H$_9$ | Cl | 1,5680($n_D^{25}$) |
| 37 | 3-Br | — | 1 | — | OC(O)OC$_4$H$_9$-i | Cl | 1,5795($n_D^{25}$) |
| 38 | 3-Br | — | 1 | — | OC(O)SC$_4$H$_9$-n | Cl | 1,6080($n_D^{25}$) |
| 39 | 3-Br | — | 1 | — | OC(O)SC$_4$H$_9$-S | Cl | 1,6085($n_D^{25}$) |
| 40 | 3-Br | — | 1 | — | OC(O)SC$_8$H$_{17}$-n | Cl | 1,5792($n_D^{25}$) |
| 41 | 4-CH$_3$O | — | 1 | — | OH | Cl | 245–247 |
| 42 | 4-CH$_3$O | — | 1 | — | OC(O)C$_6$H$_{13}$-n | Cl | 1,5598 |
| 43 | 4-CH$_3$O | — | 1 | — | OC(O)C$_7$H$_{15}$-n | Cl | 1,5539 |
| 44 | 4-CH$_3$O | — | 1 | — | OC(O)OC$_4$H$_9$-i | Cl | 58–59,5 |
| 45 | 4-CH$_3$O | — | 1 | — | OC(O)OC$_5$H$_{11}$-n | Cl | 1,5677 |
| 46 | 4-CH$_3$O | — | 1 | — | (OC(O)SC$_4$H$_9$-n | Cl | 44–53 |
| 47 | 4-CH$_3$O | — | 1 | — | Cl | Cl | 144–147 |
| 48 | 3-CF$_3$ | — | 1 | — | OH | Cl | 238–240* |
| 49 | 3-CF$_3$ | — | 1 | — | OC(O)(CH$_2$)$_5$CH$_3$ | Cl | 1,5162 |
| 50 | 3-CF$_3$ | — | 1 | — | OC(O)(CH$_2$)$_6$CH$_3$ | Cl | 1,5145 |
| 51 | 3-CF$_3$ | — | 1 | — | OC(O)OC$_4$H$_9$-i | Cl | 45–48,5 |
| 52 | 3-CF$_3$ | — | 1 | — | OC(O)OC$_5$H$_{11}$-n | Cl | 1,5161 |
| 53 | 3-CF$_3$ | — | 1 | — | OC(O)SC$_4$H$_9$-n | Cl | 36–40 |
| 54 | 3-CF$_3$ | — | 1 | — | OC(O)SC$_8$H$_{17}$-n | Cl | 1,5323 |
| 55 | 3-CF$_3$ | — | 1 | — | Cl | Cl | 80–81,5 |
| 56 | 4-F | — | 1 | — | OH | Cl | 254–260* |
| 57 | 4-F | — | 1 | — | OC(O)SC$_3$H$_7$-n | Cl | |
| 58 | 4-F | — | 1 | — | OC(O)SC$_4$H$_9$ | Cl | |
| 59 | 4-F | — | 1 | — | OC(O)SC$_4$H$_9$-s | Cl | |
| 60 | 4-F | — | 1 | — | OC(O)SC$_4$H$_9$-t | Cl | 109–111 |
| 61 | 4-F | — | 1 | — | OC(O)SC$_5$H$_{11}$-i | Cl | |
| 62 | 4-F | — | 1 | — | OC(O)OC$_5$H$_{11}$-t | Cl | 65–68 |
| 63 | 4-F | — | 1 | — | OC(O)SC$_7$H$_{15}$-n | Cl | |
| 64 | 4-F | — | 1 | — | OC(O)SC$_8$H$_{17}$-n | Cl | 1,5567 |
| 65 | 4-F | — | 1 | — | OC(O)SC$_{12}$H$_{25}$-n | Cl | 33–36 |
| 66 | 4-F | — | 1 | — | OC(O)SC$_6$H$_{11}$-c | Cl | 57–59 |
| 67 | 4-C$_2$H$_5$ | — | 1 | — | OH | Cl | 224–225 |
| 68 | 4-F | — | 1 | — | Cl | Cl | 124–127 |
| 69 | 4-Cl | 2-Cl | 1 | 1 | OH | Cl | 233–237* |
| 70 | 4-Cl | 2-Cl | 1 | 1 | OC(O)SC$_4$H$_9$-n | Cl | |
| 71 | 4-Cl | 2-Cl | 1 | 1 | Cl | Cl | 144–147 |
| 72 | 4-C$_2$H$_5$ | — | 1 | — | OC(O)SC$_8$H$_{17}$ | Cl | 1,5637 |
| 73 | 4-Cl | 3-Cl | 1 | 1 | OC(O)OCH$_2$C(CH$_3$)$_3$ | Cl | 109–111,5 |
| 74 | 4-Cl | 3NO$_2$ | 1 | 1 | OC(O)SC$_8$H$_{17}$-n | Cl | 1,5821 |
| 75 | 4-Br | 3NO$_2$ | 1 | 1 | OH | Cl | 209–212 |
| 76 | 4-C$_2$H$_5$ | — | 1 | — | OC(O)SC$_4$H$_9$-n | Cl | |
| 77 | 4-Cl | 3-Cl | 1 | 1 | OH | Cl | 239–243 |
| 78 | 4-Cl | 3-Cl | 1 | 1 | OC(O)CH$_2$CH(CH$_3$)$_2$ | Cl | 48–52 |
| 79 | 4-Cl | 3-Cl | 1 | 1 | OC(O)SC$_3$H$_7$-n | Cl | 1,6186 |
| 80 | 4-Cl | 3-Cl | 1 | 1 | OC(O)SC$_4$H$_9$-n | Cl | 1,6108 |
| 81 | 4-Cl | 3-Cl | 1 | 1 | OC(O)SC$_8$H$_{17}$-n | Cl | 1,5814 |
| 82 | 4-Br | 3NO$_2$ | 1 | 1 | OC(O)SC$_4$H$_9$ | Cl | 1,6199 |
| 83 | 4-CH$_3$ | — | 1 | — | OH | Cl | 240* |
| 84 | 4-CH$_3$ | — | 1 | — | OC(O)SC$_4$H$_9$-n | Cl | |
| 85 | 4-CH$_3$ | 3CH$_3$ | 1 | 1 | OC(O)OC$_4$H$_9$-i | Cl | |
| 86 | 4-CH$_3$S | — | 1 | — | OC(O)OC$_5$H$_{11}$-n | Cl | 65–66,5 |
| 87 | 4-CH$_3$S | — | 1 | — | OC(O)SC$_4$H$_9$-n | Cl | 1,6332 |
| 88 | 4-Cl | 3NO$_2$ | 1 | 1 | OC(O)SC$_4$H$_9$-n | Cl | 1,6073 |
| 89 | 4-Br | 3NO$_2$ | 1 | 1 | OC(O)OC$_7$H$_{15}$-n | Cl | 69–72 |
| 90 | 4-Br | 3NO$_2$ | 1 | 1 | OC(O)OC$_4$H$_9$-i | Cl | 1,5942 |
| 91 | 4-CH$_3$ | 2CH$_3$ | 1 | 1 | Cl | Cl | 92–100 |
| 92 | 4(5)NO$_2$ | 2(3)NO$_2$ | 1 | 1 | OC(O)OCH$_2$CH(CH$_3$)$_2$ | Cl | — |
| 93 | 4-Cl,3-Cl | 2-Cl | 2 | 1 | OH | Cl | 230–237 |
| 94 | 4-Cl,3-Cl | 2-Cl | 2 | 1 | OC(O)SC$_4$H$_9$-n | Cl | |
| 95 | 4-C$_4$H$_9$O | — | 1 | — | OC(O)(CH$_2$)$_5$CH$_3$ | Cl | |
| 96 | 4-CH$_3$O | 3NO$_2$ | 1 | 1 | Cl | Cl | 213–215 |
| 97 | 4-C$_6$H$_5$O | — | 1 | — | OH | Cl | 197–201* |
| 98 | 4-C$_6$H$_5$O | — | 1 | — | OC(O)OC$_5$H$_{11}$-n | Cl | 1,5901 |
| 99 | 4-C$_6$H$_5$O | — | 1 | — | OC(O)SC$_4$H$_9$-n | Cl | 1,6179 |
| 100 | 4-Br | 3NO$_2$ | 1 | 1 | OC(O)SC$_8$H$_{17}$-n | Cl | 1,5895 |
| 101 | 4-Cl | 2-Cl | 1 | 1 | OC(O)SC$_4$H$_9$-n | Cl | |
| 102 | 4-F | — | 1 | — | OC(O)SC$_5$H$_{11}$-n | Cl | |
| 103 | 4-Br | 3NO$_2$ | 1 | 1 | OC(O)CH(C$_2$H$_5$)C$_4$H$_9$ | Cl | 69–72 |
| 104 | 4-CH$_3$S | — | 1 | — | OH | Cl | 230–231 |
| 105 | 4-CH$_3$SO$_2$ | — | 1 | — | OH | Cl | 203–212 |

-continued

| Comp. | $R_1$ | $R_2$ | n | m | $R_3$ | X | M.P.(°C.)/$n_D^{20}$ |
|---|---|---|---|---|---|---|---|
| 106 | 4-$CH_3S$ | — | 1 | — | Cl | Cl | 120–121 |
| 107 | 2-$CH_3$ | 5$CH_3$ | 1 | 1 | Cl | Cl | 100–101 |
| 108 | 4(5)$NO_2$ | 2(3)$NO_2$ | 1 | 1 | OH | Cl | 250–252 |
| 109 | 4(5)$NO_2$ | 2(3)$NO_2$ | 1 | 1 | OC(O)O$C_5H_{11}$ | Cl | |
| 110 | 4(5)$NO_2$ | 2(3)$NO_2$ | 1 | 1 | OC(O)N$(CH_3)_2$ | Cl | |
| 111 | 4Cl,3Cl | 2Cl | 2 | 1 | Cl | Cl | 115–118 |
| 112 | 4-$C_4H_9O$ | — | 1 | — | OC(O)S$C_6H_{11}$-c | Cl | 1,5882 |
| 113 | 4-$C_4H_9O$ | — | 1 | — | OC(O)S$C_8H_{17}$-n | Cl | 50–53,5 |
| 114 | 4-$C_4H_9O$ | — | 1 | — | OC(O)S$C_{12}H_{25}$-n | Cl | 50–56 |
| 115 | 4-$C_4H_9O$ | — | 1 | — | OC(O)N$(CH_3)_2$ | Cl | 97,5–99 |
| 116 | 4-$C_4H_9O$ | — | 1 | — | Cl | Cl | 62–63 |
| 117 | 4-$CH_3O$ | 3$NO_2$ | 1 | 1 | OH | Cl | 250–254* |
| 118 | 4-$C_6H_5O$ | — | 1 | — | Cl | Cl | 129–133 |
| 119 | 3-$NH_2$ | — | 1 | — | OH | Cl | 185–188 |
| 120 | 4-$C_6H_{11}$-c | — | 1 | — | OH | Cl | 225–235 |
| 121 | 4-$CH_3$ | 4$CH_3$ | 1 | 1 | OH | Cl | 222–224 |
| 122 | 4-$C_2H_5$ | — | 1 | — | OC(O)O$CH_2C(CH_3)_3$ | Cl | 70–71,5 |
| 123 | 3-$CH_3$ | 4$CH_3$ | 1 | 1 | OC(O)$C_5H_{11}$-n | Cl | |
| 124 | 3-$CH_3$ | 4$CH_3$ | 1 | 1 | Cl | Cl | 90–92 |
| 125 | 3-Cl | 4Cl | 1 | 1 | Cl | Cl | 150–152 |
| 126 | 4-$CH_3$—$SO_2$ | — | 1 | — | OC(O)S$C_4H_9$-n | Cl | 99–102 |
| 127 | 5-$CH_3$ | 2$CH_3$ | 1 | 1 | OH | Cl | 163–170 |
| 128 | 4(5)$NO_2$ | 2(3)$NO_2$ | 1 | 1 | Cl | Cl | 161–166 |
| 129 | 4Cl,3Cl | 2Cl | 2 | 1 | OC(O)S$C_8H_{17}$-n | Cl | |
| 130 | 4-$C_4H_9O$ | — | 1 | — | OH | Cl | 216–218 |
| 131 | 4-$C_4H_9O$ | — | 1 | — | OC(O)O$C_5H_{11}$-n | Cl | 37–39 |
| 132 | 4-$C_4H_9O$ | — | 1 | — | OC(O)O$C_4H_9$-i | Cl | 68–70 |
| 133 | 4-$C_4H_9O$ | — | 1 | — | OC(O)S$C_4H_9$-n | Cl | 52–54 |
| 134 | 3$NO_2$5$NO_2$ | 4$CH_3O$ | 2 | 1 | OH | Cl | 280 |
| 135 | 4-$C_6H_{11}$-c | — | 1 | — | OC(O)S$C_4H_9$-n | Cl | 1,5878 |
| 136 | 4-$C_6H_{11}$-c | — | 1 | — | Cl | Cl | 115–118 |
| 137 | 4Cl | — | 1 | — | OC(O)S$CH_2CH_2C_6H_5$ | Cl | 1,6303 |
| 138 | 4-Cl | 3$NO_2$ | 1 | 1 | OH | Cl | 208–211 |
| 139 | 3-$NO_2$ | — | 1 | — | Cl | Cl | 186–191 |
| 140 | 3-$NO_2$ | — | 1 | — | OH | Cl | 246–249 |
| 141 | 3-$NO_2$ | — | 1 | — | OC(O)O$C_5H_{11}$-n | Cl | |
| 142 | 4-OH | — | 1 | — | OH | Cl | 280* |
| 143 | 4-Br | — | 1 | — | OC(O)O$CH_2C(CH_3)_3$ | Cl | 114–116 |
| 144 | 4-CN | — | 1 | — | Cl | Cl | 210–222 |
| 145 | 4-CN | — | 1 | — | OH | Cl | 286–290 |

*Decomposition

EXAMPLE A 20 parts of Compound No. 9 are melted and, in the liquid state, intimately mixed with 20 parts of precipitated ground silica, 50 parts of kieselguhr, 3 parts of the sodium salt of diisobutylnaphthalenesulfonic acid and 7 parts of sodium ligninsulfonate, and the mixture is ground for 1 hour in a planet ball mill. This gives a wettable powder which disperses readily in water and is therefore suitable for preparing a biologically active spray mixture.

EXAMPLE B 40 parts of Compound No. 57, a pale brown oil, are intimately mixed with 40 parts of precipitated ground silica, 10 parts of kieselguhr, 4 parts of chalk, 3 parts of the sodium salt of diisobutylnaphthalenesulfonic acid and 3 parts of sodium N-oleoyl-N-methyltauride, and the mixture is ground intimately in a planet ball mill. This gives a wettable powder which disperses readily in water and is therefore suitable for preparing a biologically active spray mixture.

EXAMPLE C 10 parts of Compound No. 19 are intimately mixed with 10 parts of precipitated ground silica, 70 parts of Attaclay, 2 parts of the sodium salt of diisobutylnaphthalenesulfonic acid, 1 part of sodium N-oleoyl-N-methyltauride and 7 parts of sodium ligninsulfonate, and the mixture is ground for 1 hour in a planet ball mill. This gives a wettable powder which disperses readily in water and is therefore suitable for preparing a biologically active spray mixture.

EXAMPLE D 50 parts of Compound No. 36 are intimately mixed with 45 parts of precipitated ground silica, 2 parts of the sodium salt of diisobutylnaphthalenesulfonic acid and 3 parts of sodium N-oleoyl-N-methyltauride, and the mixture is ground for 1 hour in a planet ball mill. This gives a wettable powder which disperses readily in water and is therefore suitable for preparing a biologically active spray mixture.

EXAMPLE E 40 parts of Compound No. 64 are intimately mixed with 45 parts of precipitated ground silica, 9 parts of finely ground chalk, 3 parts of the sodium salt of diisobutylnaphthalenesulfonic acid and 3 parts of sodium N-oleoyl-N-methyltauride, and the mixture is ground for 1 hour in a planet ball mill. This gives a wettable powder which disperses readily in water and is therefore suitable for preparing a biologically active spray mixture.

EXAMPLE F 25 parts of Compound No. 53 are dissolved in 65 parts of Solvesso 100 (aromatic solvent, consisting mainly of trimethylbenzenes), and 10 parts of an emulsifier mixture, consisting of calcium dodecylbenzenesulfonate and a polyoxyethylene sorbitan tall oil ester, are added. This gives an emulsifiable concentrate which is suitable for preparing a biologically active spray mixture.

EXAMPLE G 60 parts of Compound No. 52 are dissolved in a mixture of 20 parts of xylene and 10 parts of butyrolactone, and 10 parts of an emulsifier mixture, consisting of calcium dodecylbenzenesulfonate and a polyoxyethylene sorbitan tall oil ester, are added. This gives an emulsifiable concentrate which is suitable for preparing a biologically active spray mixture.

EXAMPLE H 40 parts of Compound No. 64 are dissolved in a mixture of 30 parts of Solvesso 100 and 20 parts of cyclohexanone, and 10 parts of an emulsifier mixture, consisting of calcium dodecylbenzenesulfonate and a polyethoxylated castor oil, are added. This gives an emulsifiable concentrate which is suitable for preparing a biologically active spray mixture.

EXAMPLE I 10 parts of Compound No. 22 are dissolved in 80 parts of Solvesso 100, and 10 parts of an emulsifier mixture, consisting of calcium dodecylbenzenesulfonate and a polyethoxylated nonylphenol, are added. This gives an emulsifiable concentrate which is suitable for biologically active spray mixture.

EXAMPLE J

Herbicidal action

A particular amount of active substance (see corresponding tests) was applied by the post-emergence method (3–5 leaf stage of the test plants). The experiments were evaluated following the key of Table 1. The experiments were scored visually 2–3 times (1–9 scale). The values given are averages of all assessments. The codes of the test plants used in the following text are explained in Table 2.

TABLE 1

| | EWRC Scale 1-9: | |
|---|---|---|
| Value | Herbicidal action | in % |
| 1 | excellent | 100 |
| 2 | very good | 97.5 |
| 3 | good | 95.0 |
| 4 | satisfactory | 90.0 |
| 5 | sufficient | 85.0 |
| 6 | insufficient | 80.0 |
| 7 | poor | 75.0 |
| 8 | very poor | 65.0 |
| 9 | no action | 32.5 |

TABLE 2

| Codes of the test plants used | | |
|---|---|---|
| Code | Latin name | English name |
| AMARE | *Amaranthus retofluxus* | redroot pigweed |
| ANTAR | *Anthemis arvensis* | corn camomile |
| CENAR | *Centaurea arvensis* | cornflower |
| CHEFI | *Chenopodium ficifolium* | fig-leaved goosefoot |
| ECHCG | *Echinochloa crus-galli* | common barnyard grass |
| GALAP | *Galium aparine* | catchweed bedstraw |
| MERAN | *Mercurialis annua* | annual mercury |
| LAPCO | *Lapsana communis* | nipplewort |
| PANMI | *Panicum milliaceum* | proso millet |
| SETGL | *Setaria glauca* | yellow foxtail |
| SOLAM | *Solanum americanum* | American nightshade |
| SOLNI | *Solanum nigrum* | black nightshade |
| STEME | *Stellaria media* | common chickweed |

Standard: 6-Chloro-3-phenylpyridazin-4-yl-s-octyl thio-carbonate
A.I.: Active Ingredient
a) Nopon (oil additive)

EXAMPLE K

| Compound | Dosage g of A.I./ha | Herbicidal action (1-9 scale) GALAP | STEME | LAPCO | ANTAR | ø |
|---|---|---|---|---|---|---|
| Standard | 300 | 1.7 | 4.3 | 1.7 | 1.7 | 2.35 |
| Standard + a | 300 + 5.01 | 1.7 | 5.0 | 1.7 | 1.3 | 2.42 |
| Comp. 64 | 300 | 1.3 | 3.3 | 1.7 | 1.3 | 1.9 |
| Comp. 64 + a | 300 + 5.01 | 1.0 | 2.3 | 1.7 | 1.3 | 1.58 |

In the above experiment, the compound mentioned in this example performs better than the given standard.

Similar profiles of action were ascertained with analogous compounds.

EXAMPLE L

| Compound | Dosage g of A.I./ha | Herbicidal action (1-9 scale) SOLNI | CHEFI | MERAN | AMARE | ø |
|---|---|---|---|---|---|---|
| Standard | 300 | 1.0 | 1.0 | 3.0 | 1.5 | 1.63 |
| | 150 | 1.0 | 1.0 | 4.0 | 2.0 | 2.0 |
| Comp. 64 | 300 | 1.0 | 1.0 | 2.0 | 1.5 | 1.38 |
| | 150 | 1.0 | 1.0 | 2.0 | 1.5 | 1.38 |

Similar values were achieved with analogous compounds.

EXAMPLE M

| Compound | Product kg/ha | Herbicidal action (1-9 scale) GALAP | STEME | LAPCO | ANTAR | ø |
|---|---|---|---|---|---|---|
| Standard | 0.6 | 5.0 | 7.0 | 1.0 | 3.5 | 4.13 |
| | 0.4 | 5.0 | 7.0 | 3.5 | 6.0 | 5.38 |
| Comp. 64 | 0.6 | 1.0 | 4.5 | 1.0 | 1.0 | 1.8 |
| | 0.4 | 1.0 | 5.0 | 1.0 | 2.5 | 2.38 |

Similar values were achieved with analogous compounds.

EXAMPLE N

Herbicidal activity against Solanum americanum (SOLAM)=American nightshade.

| Compound | Dosage in g of A.I./ha | Herbicidal action (1–9 scale) SOLAM |
|---|---|---|
| Compound 64 | 300 | 2.7 |
| | 200 | 5.7 |
| | 100 | 6.7 |

EXAMPLE O

Herbicidal action against panic grasses

| Compound | Product kg/ha | Herbicidal action (%) | | | |
|---|---|---|---|---|---|
| | | ECHGG | SETGL | PANMI | ∅ |
| Standard | 0.5 | 10.3 | 44.2 | 0 | 18.17 |
| | 0.75 | 26.9 | 44.3 | 0 | 23.7 |
| Comp. 64 | 1.125 | 64.7 | 49.5 | 26.7 | 46.97 |
| | 1.688 | 72.1 | 63.5 | 65.6 | 67.1 |

In all cases, Compound 64 performs better than the values of the standard.

EXAMPLE P

| Compound | Dosage in g of A.I./ha | Herbicidal action (1–9 scale) | | | | |
|---|---|---|---|---|---|---|
| | | SOLNI | CHEFI | MERAN | AMARE | ∅ |
| Standard | 300 | 1.3 | 2.9 | 1.3 | 2.4 | 1.98 |
| Comp. 57 | 300 | 1.0 | 3.1 | 1.0 | 1.1 | 1.55 |
| Comp. 59 | 300 | 1.0 | 2.9 | 1.0 | 1.0 | 1.48 |
| Comp. 100 | 300 | 1.0 | 2.9 | 1.3 | 1.1 | 1.58 |
| Comp. 62 | 300 | 1.0 | 3.9 | 1.0 | 2.4 | 2.1 |
| Comp. 63 | 300 | 1.0 | 3.0 | 1.0 | 2.6 | 1.9 |
| Comp. 64 | 300 | 1.0 | 2.7 | 1.1 | 2.7 | 1.88 |

EXAMPLE Q

| Compound | Dosage in g of A.I./ha | Herbicidal action (1–9 scale) | | | | |
|---|---|---|---|---|---|---|
| | | ANTAR | CENAR | LAPCO | GALAP | ∅ |
| Standard | 300 | 1.3 | 2.2 | 1.1 | 2.1 | 1.68 |
| Comp. 9 | 300 | 1.0 | 2.7 | 1.0 | 2.0 | 1.68 |
| Comp. 10 | 300 | 1.0 | 2.6 | 1.0 | 2.1 | 1.68 |
| Comp. 11 | 300 | 1.0 | 2.6 | 1.0 | 2.0 | 1.65 |

EXAMPLE R

| Compound | Dosage in g of A.I./ha | Herbicidal action (1–9 scale) | | | | |
|---|---|---|---|---|---|---|
| | | ANTAR | CENAR | LAPCO | GALAP | ∅ |
| Standard | 200 | 1.0 | 2.4 | 1.7 | 2.0 | 1.78 |
| Comp. 5 | 200 | 1.0 | 3.0 | 1.3 | 2.0 | 1.83 |

EXAMPLE S

| Compound | Dosage in g of A.I./ha | Herbicidal action (1–9 scale) | | | | |
|---|---|---|---|---|---|---|
| | | ANTAR | CENAR | LAPCO | GALAP | ∅ |
| Standard | 1000 | 1.1 | 5.0 | 1.3 | 2.0 | 2.35 |
| Comp. 99 | 500 | 1.0 | 1.9 | 1.0 | 3.7 | 1.9 |

EXAMPLE T

| Compound | Dosage in g of A.I./ha | Herbicidal action (1–9 scale) | | | | |
|---|---|---|---|---|---|---|
| | | ANTAR | CENAR | LAPCO | GALAP | ∅ |
| Standard | 500 | 1.3 | 2.7 | 2.2 | 1.4 | 1.9 |
| Comp. 36 | 500 | 1.0 | 2.8 | 2.4 | 1.0 | 1.8 |
| Comp. 22 | 500 | 1.0 | 3.2 | 1.0 | 2.3 | 1.88 |
| Comp. 5 | 500 | 1.0 | 3.3 | 1.0 | 2.3 | 1.9 |

EXAMPLE U

| Compound | Dosage in g of A.I./ha | Herbicidal action (1–9 scale) | | | | |
|---|---|---|---|---|---|---|
| | | ANTAR | CENAR | LAPCO | GALAP | ∅ |
| Standard | 750 | 3.9 | 5.3 | 2.9 | 2.9 | 3.75 |
| Comp. 54 | 750 | 2.7 | 2.9 | 2.7 | 3.5 | 2.95 |
| Comp. 53 | 750 | 2.6 | 4.7 | 2.8 | 4.3 | 3.6 |

What is claimed is:

1. A method for controlling weeds which comprises applying to said weeds or to their environment at least 150 gram per hectare of 6-chloro-3-(4'-fluorophenyl)-pyridazin-4-yl-S-octylthiocarbonate or a salt thereof with or without extenders and/or surface active agents.

2. A method according to claim 1 which comprises applying a herbicidal composition consisting essentially of 6-chloro-3-(4'-fluorophenyl)-pyridazin-4-yl-S-octylthiocarbonate or a salt thereof, extenders and/or surface active agent.

* * * * *